(12) United States Patent
Hanebuchi et al.

(10) Patent No.: US 9,138,138 B2
(45) Date of Patent: Sep. 22, 2015

(54) OPHTHALMIC APPARATUS AND RECORDING MEDIUM HAVING OPHTHALMIC PROGRAM STORED THEREIN

(71) Applicant: NIDEK CO., LTD., Aichi (JP)

(72) Inventors: Masaaki Hanebuchi, Aichi (JP); Michihiro Takii, Aichi (JP); Masakazu Endo, Aichi (JP)

(73) Assignee: NIDEK CO., LTD., Aichi (JP)

( * ) Notice: Subject to any disclaimer, the term of this patent is extended or adjusted under 35 U.S.C. 154(b) by 250 days.

(21) Appl. No.: 13/684,284

(22) Filed: Nov. 23, 2012

(65) Prior Publication Data

US 2013/0135582 A1    May 30, 2013

(30) Foreign Application Priority Data

Nov. 30, 2011  (JP) ................................. 2011-263095
Oct. 26, 2012  (JP) ................................. 2012-236178

(51) Int. Cl.
  *A61B 3/14*   (2006.01)
  *A61B 3/00*   (2006.01)
  *A61B 3/10*   (2006.01)

(52) U.S. Cl.
  CPC ............. *A61B 3/0016* (2013.01); *A61B 3/0025* (2013.01); *A61B 3/1015* (2013.01)

(58) Field of Classification Search
  USPC ........................................................ 351/206
  See application file for complete search history.

(56) References Cited

U.S. PATENT DOCUMENTS

2003/0107708 A1   6/2003   Isogai
2008/0231809 A1   9/2008   Haigis

FOREIGN PATENT DOCUMENTS

JP      2003169778 A    6/2003
JP      2007505716 A    3/2007

*Primary Examiner* — Jack Dinh
(74) *Attorney, Agent, or Firm* — Rankin, Hill & Clark LLP

(57) ABSTRACT

An ophthalmic apparatus includes: an input unit configured to obtain corneal incision information that is information on a corneal incision to be formed on a cornea of an examinee's eye; an imaging device configured to image an examinee's eye image; and a controller. The controller is configured to calculate first wavefront aberration distribution that is wavefront aberration distribution of the cornea before incision on the examinee's eye based on the examinee's eye image, obtain incision aberration information corresponding to the corneal incision information; calculate second wavefront aberration distribution that is wavefront aberration distribution after formation of the incision based on the first wavefront aberration distribution and the incision aberration information, and output guide information that guides an intraocular lens surgery based on the second wavefront aberration distribution.

15 Claims, 4 Drawing Sheets

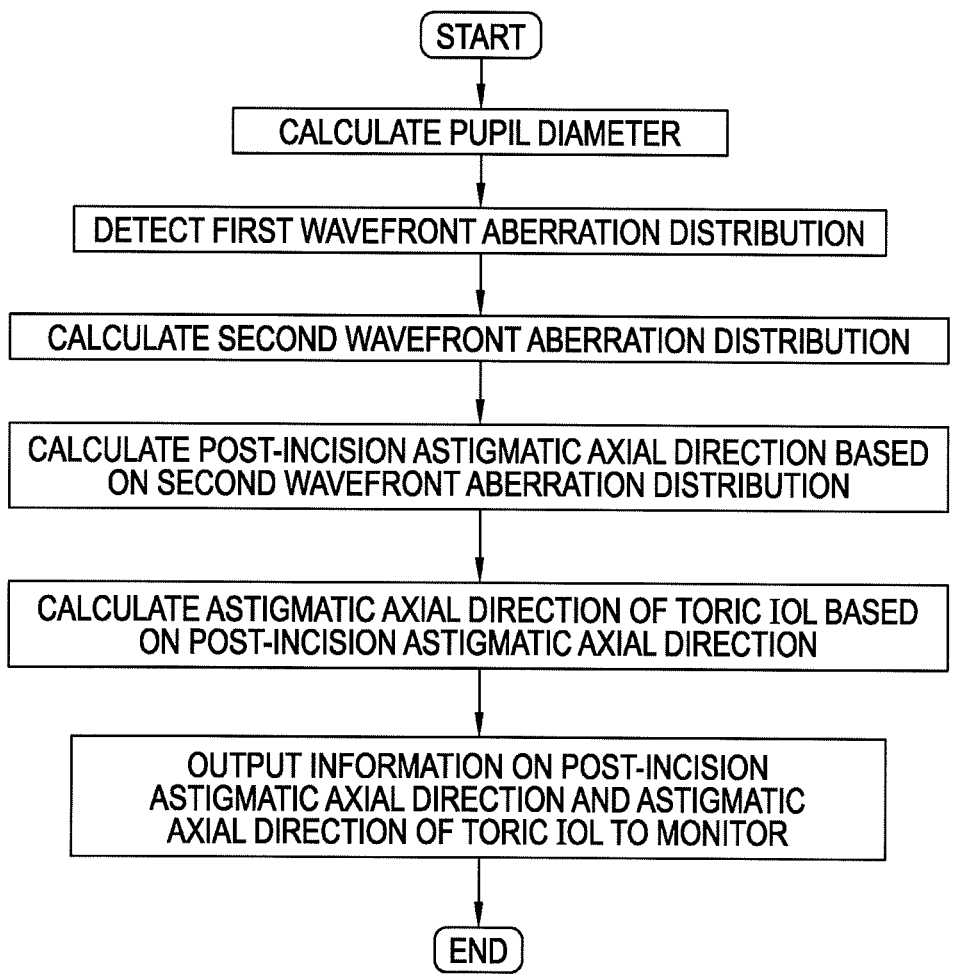

PUPIL
IRIS
L

HORIZONTAL SYNCHRONIZATION SIGNAL

OPHTHALMIC APPARATUS AND RECORDING MEDIUM HAVING OPHTHALMIC PROGRAM STORED THEREIN

CROSS-REFERENCE TO RELATED APPLICATION

This application is based on Japanese Patent Application Nos. 2011-263095 filed on Nov. 30, 2011 and 2012-236178 filed on Oct. 26, 2012 with the Japan Patent Office, the entire contents of which are hereby incorporated by reference.

BACKGROUND

1. Technical Field

The present disclosure relates to an ophthalmic apparatus and a recording medium having an ophthalmic program stored therein.

2. Related Art

An ophthalmic apparatus determines diopter power of an intraocular lens (hereinafter referred to as IOL) to be inserted in an examinee's eye by a cataract surgery, for example. In the cataract surgery, in order to determine (calculate) power (hereinafter referred to as diopter power) of the IOL, eye characteristic data specific to the examinee such as corneal refractive power and the ocular axial length of the examinee's eye are measured after removal of a crystalline lens nucleus. Based on these data, the diopter power of the IOL is calculated in accordance with an IOL calculating formula made by logic. Examples of a known IOL calculating formula include an SRK formula and an SRK/T formula (refer to JP-T-2007-505716).

In recent years, as one of the IOLs, a TORIC-Intraocular lens (TORIC IOL) for astigmatism correction is known. In a case of prescribing such a TORIC IOL, the corneal curvature and the corneal astigmatic axis are calculated by a keratometer (for example, refer to JP-A-2003-169778). Also, the ocular axial length is calculated by an ocular axial length measurement apparatus. Based on these calculation results, a TORIC IOL to be inserted is determined.

Subsequently, a surgeon uses a dedicated member to place a first mark on an examinee's eye in the direction of the horizontal axis thereof. The surgeon also places a second mark at a position corresponding to the astigmatic axis (strong principal meridian direction) of the examinee's eye with reference to the first mark. The surgeon inserts the intraocular lens into the eye so that the second mark and the astigmatic axis of the TORIC-Intraocular lens correspond to each other.

SUMMARY

An ophthalmic apparatus includes: an input unit configured to obtain corneal incision information that is information on a corneal incision to be formed on a cornea of an examinee's eye; an imaging device configured to image an examinee's eye image; and a controller. The controller is configured to calculate first wavefront aberration distribution that is wavefront aberration distribution of the cornea before incision on the examinee's eye based on the examinee's eye image, obtain incision aberration information corresponding to the corneal incision information; calculate second wavefront aberration distribution that is wavefront aberration distribution after formation of the incision based on the first wavefront aberration distribution and the incision aberration information, and output guide information that guides an intraocular lens surgery based on the second wavefront aberration distribution.

BRIEF DESCRIPTION OF DRAWINGS

FIG. 2 illustrates a flowchart of control operation in the present apparatus;

DETAILED DESCRIPTION

Figure 1:
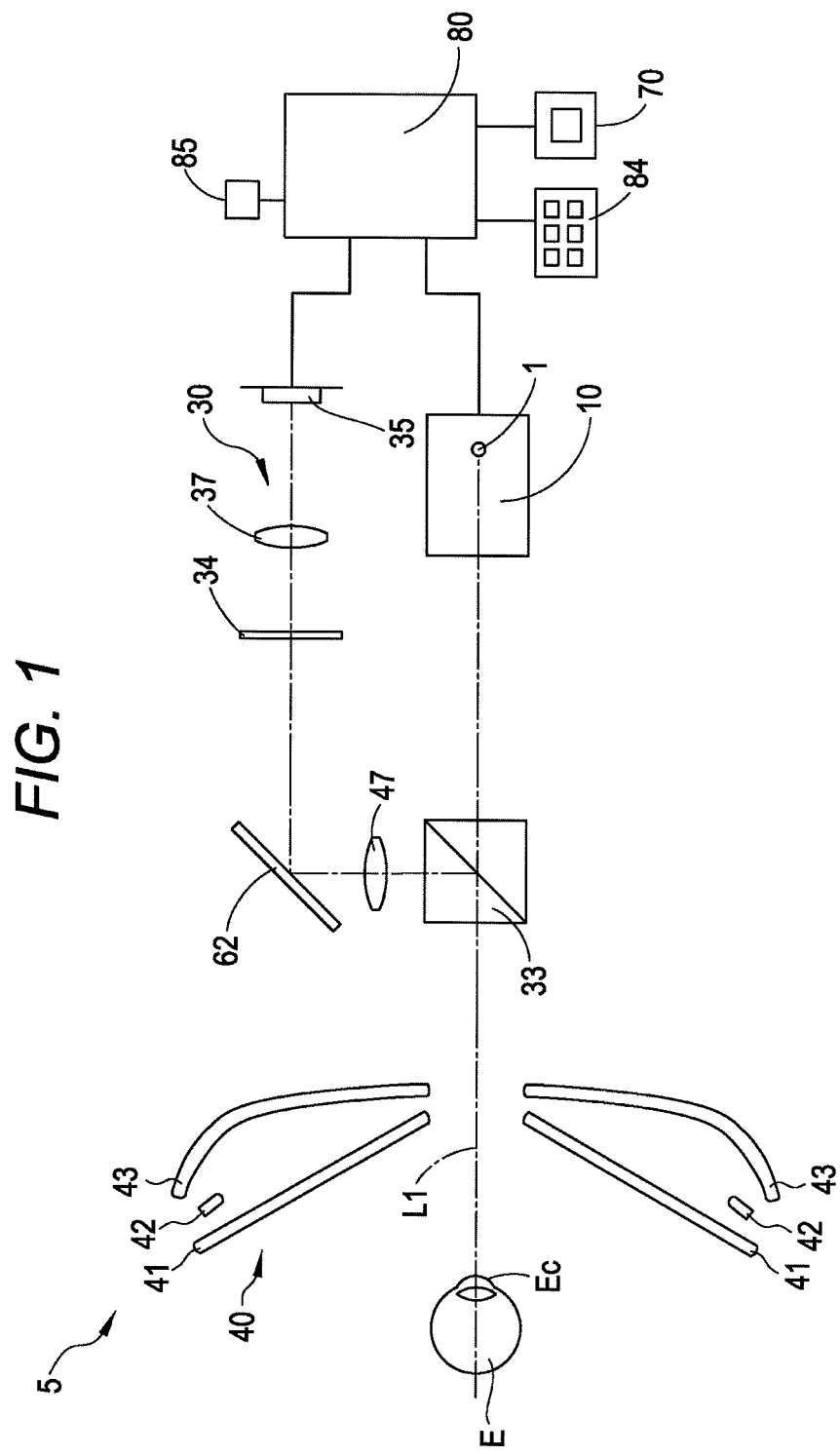
FIG. 1 illustrates a schematic configuration of an optical system and a control system of an ophthalmic apparatus (present apparatus) according to an embodiment of the present disclosure.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

When the TORIC IOL is inserted in the eye in an out-of-alignment state of the direction of the astigmatic axis of the examinee's eye (such as the strong principal meridian direction of astigmatism) and the direction of the astigmatic axis of the TORIC IOL, the examinee's eye may be insufficiently corrected. Such misalignment is attributable to many factors.

For example, in the surgery, a cornea is incised to make a corneal incision for insertion of the IOL. The corneal shape is changed by this incision. This causes change in aberration all over the entire cornea before and after the incision. Thus, the wavefront aberration distribution (wavefront aberration state) measured before the incision is changed after the incision. Accordingly, when the IOL is inserted in accordance with the wavefront aberration distribution measured before the incision, the examinee's eye cannot be corrected sufficiently in some cases due to the misalignment caused by change in the direction of the astigmatic axis.

On this occasion, parameters to be used in diopter power calculation may be both the direction of the astigmatic axis before the surgery and deformation (induced astigmatism) of the cornea by the corneal incision.

However, the deformation of the cornea by the corneal incision is not axisymmetric around the center of a pupil. The influence of this deformation leads to high-order aberration. Change in aberration due to the corneal incision occurs in the entire cornea. Thus, correction accuracy with the TORIC IOL may be hardly enhanced by just correcting change of the astigmatic axis, which is partial information of the corneal shape.

An object of the present disclosure is to provide an ophthalmic apparatus that improves correction accuracy with a TORIC IOL.

An ophthalmic apparatus includes: an input unit configured to obtain corneal incision information that is information on a corneal incision to be formed on a cornea of an examinee's eye; an imaging device configured to image an examinee's eye image; and a controller. The controller is configured to calculate first wavefront aberration distribution that is wavefront aberration distribution of the cornea before incision on the examinee's eye based on the examinee's eye image, obtain incision aberration information corresponding to the corneal incision information; calculate second wavefront aberration distribution that is wavefront aberration distribution after formation of the incision based on the first wavefront aberration distribution and the incision aberration information, and output guide information that guides an intraocular lens surgery based on the second wavefront aberration distribution.

The ophthalmic apparatus attains improvement in correction accuracy with an intraocular lens (such as a TORIC IOL) can be improved.

Hereinafter, embodiments of the present disclosure will be described with reference to the drawings. FIG. 1 illustrates a schematic configuration of an optical system and a control system of an ophthalmic apparatus according to the present embodiment (present apparatus). It is to be noted that, in the present embodiment, the axial direction of an examinee's eye (eye E) is referred to as the Z direction, the horizontal direction thereof is referred to as the X direction, and the vertical direction thereof is referred to as the Y direction. An optical system described below is built in a housing (not shown). Also, the housing is moved three-dimensionally with respect to the examinee's eye E via an operating member (input unit such as a joystick) by a known alignment shifting mechanism.

A schematic configuration of the present apparatus will be described. The present apparatus is an ophthalmic apparatus for use in an intraocular lens inserting surgery, for example. As illustrated in FIG. 1, the present apparatus includes an ocular axial length measuring unit 10 and a corneal shape measuring unit 5.

The ocular axial length measuring unit 10 is used to measure the ocular axial length of the eye E. The corneal shape measuring unit 5 is used to measure the corneal shape.

The corneal shape measuring unit (a pupil diameter measuring unit or a corneal aberration measuring unit) 5 includes a placido ring projecting optical system 40 and an imaging optical system 30. The placido ring projecting optical system 40 includes a placido plate 41, a visible light source 42, and a reflective plate 43. The placido plate 41 has multiple annular targets. The visible light source 42 illuminates the placido plate 41 from the backside. The imaging optical system 30 includes a dichroic mirror 33, an objective lens 47, a mirror 62, a filter 34, an imaging lens 37, and a two-dimensional imaging device 35 as an imaging unit. The two-dimensional imaging device 35 is arranged at a position to be approximately conjugated with an anterior segment. The imaging optical system 30 is also used as an anterior segment front imaging optical system. The imaging optical system 30 is also used to measure the pupil diameter of the examinee's eye.

The ocular axial length measuring unit 10 includes a light projecting optical system and a light receiving optical system. The light projecting optical system includes a measurement light source 1 that emits low coherent light. The light projecting optical system splits the light emitted from the measurement light source 1 into measurement light and reference light. The light projecting optical system emits at least the measurement light to the examinee's eye. Also, the light receiving optical system synthesizes reflected light from the examinee's eye with the reference light to generate synthetic light. The light receiving optical system makes this synthetic light enter a light receiving device. The ocular axial length is calculated based on a light receiving signal output from the light receiving device and timing at which interference light has been detected by the light receiving device. It is to be noted that, in the present apparatus, the measurement light source 1 of the ocular axial length measuring unit 10 is also used as a sight fixation light.

Also, for example, the dichroic mirror 33 transmits a large part of fundus reflected light, which is obtained by reflection of light emitted from the light source 1 on a fundus. Subsequently, the light receiving device of the ocular axial length measuring unit 10 receives the light passing through the dichroic mirror 33.

Next, the control system will be described. A controller 80 controls the entire apparatus and calculates measurement results. The controller 80 is connected to the light source 1, the light source 42, the imaging device 35, a monitor 70, a memory 85, an operating unit (input unit) 84, and the like. The controller 80 calculates measurement data on the cornea of the examinee's eye to obtain various kinds of information. Examples of these measurement data include corneal curvature distribution of the corneal shape, a three-dimensional shape on the surface of the cornea of the examinee's eye (distribution of the height of the cornea of the examinee's eye in the measurement light axis L1 direction), and corneal refractive power distribution. The calculation results by the controller 80 are displayed on the monitor 70. The operating unit 84 has various switches to input instruction signals in the controller 80.

Hereinafter, control operation in the present apparatus will be described. FIG. 2 is a flowchart illustrating control operation in the present apparatus. The present apparatus effectively assists insertion of an IOL using a corneal shape measurement result. In the following description, a TORIC IOL for astigmatism correction is taken as an example. Hereinafter, as an assist of insertion of the IOL, a position in the eye where the IOL is to be arranged is calculated. Accordingly, an axial direction position (axial direction) of the examinee's eye after incision (after formation of an incision) is calculated with high accuracy before the intraocular lens inserting surgery. Hereinafter, a method for such calculation will be described.

Measurement of Corneal Shape

First, the controller 80 measures a corneal shape by the corneal shape measuring unit 5. In measurement of the corneal shape, the light source 42 is lit to project a placido ring onto the cornea. At this moment, the examinee (eye E) is made to gaze fixedly at the sight fixation light. An anterior segment image (examinee's eye image) is captured by the imaging device 35 and is displayed on the monitor 70. A surgeon moves the apparatus in up-down, right-left, and front-back directions using an operating unit such as a joystick (not shown) while looking at an alignment state of the anterior segment image displayed on the monitor 70. Then, the surgeon places the apparatus at a predetermined position relative to the eye E. Consequently, alignment of the present apparatus is completed.

After completion of the alignment, a trigger signal to start measurement is output automatically or manually. By doing so, a placido ring image (placido image) captured by the imaging device 35 is stored in the memory 85.

Subsequently, the controller 80 calculates the pupil diameter based on the obtained placido image (anterior segment image). Hereinafter, a method of detecting the pupil diameter by deriving edge positions of the pupil from the anterior segment image will be described with reference to FIGS. 3A to 3D.

Figure 3A:
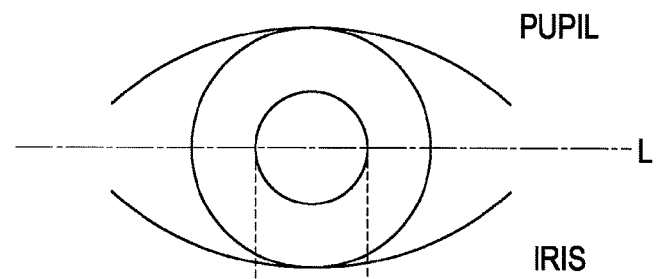
FIGS. 3A to 3D illustrate a method of detecting a pupil diameter.
Figure 3B:
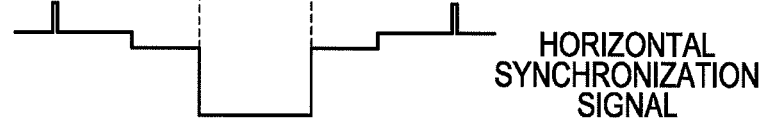
Figure 3C:
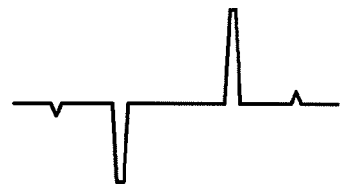
Figure 3D:
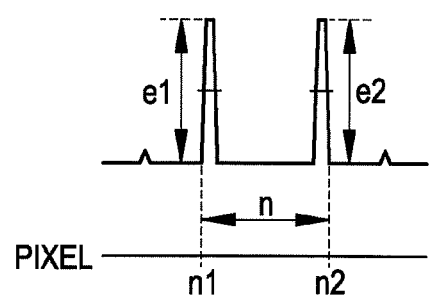

FIG. 3A illustrates a state of the anterior segment image (pupil image) stored in the memory 85. FIG. 3B illustrates an image signal along a scanning line L. To determine a boundary (edge) between a pupil (dark part) and an iris (bright part), differential processing is first performed on waveform of the image signal illustrated in FIG. 3B. This processing gives signal waveform illustrated in FIG. 3C. This signal waveform contains positive and negative peaks. Additionally, this signal waveform is squared to obtain signal waveform having positive peaks as illustrated in FIG. 3D. As illustrated in FIG. 3D, this signal waveform contains a left peak having the height e1 and a right peak having the height e2. Edges of these peaks are defined as points that are ½ of the respective heights (amplitude). In this case, a coordinate position of the edge of the right peak on the scanning line L is a pixel position n1 while a coordinate position of the edge of the left peak on the scanning line L is a pixel position n2.

Thereafter, the number of pixels n between the pixel positions n1 and n2 is derived. Here, the length of one pixel is K, and the optical magnification is P. In this case, the distance between the pixel positions n1 and n2 (pupil diameter PS') is derived from the following formula.

$$PS' = n*K/P$$

In this formula, values of K and P are known values unique to the present apparatus. Thus, by deriving the number of pixels n described above, the pupil diameter PS' is obtained.

Thereafter, a position of the pupil center is detected based on outline information of the pupil. With reference to this pupil center, pupil diameters in the respective meridian directions are calculated. It is to be noted that, in calculation of the pupil diameters, the controller 80 may photograph the pupil both in a bright field state and in a dark field state and calculate pupil diameters in the respective states. Alternatively, the controller 80 may calculate a pupil diameter either in a bright field state or in a dark field state.

After calculation of the pupil diameter, the controller 80 calculates measurement data on the cornea of the examinee's eye based on the obtained placido image (anterior segment image). By doing so, the controller 80 obtains various kinds of information (detailed information). Examples of these measurement data include corneal curvature distribution, a three-dimensional shape on the surface of the cornea of the examinee's eye (distribution of the height of the cornea of the examinee's eye in the measurement light axis L1 direction), and corneal refractive power distribution. Also, the controller 80 compares the distribution of the height of the cornea of the examinee's eye with the distribution of the height of the cornea in a case where the aberration is 0. Based on information on the difference between these kinds of distribution, the controller 80 derives wavefront aberration distribution of a cornea region corresponding to the pupil diameter calculated as described above. This wavefront aberration distribution is wavefront aberration distribution before formation of the corneal incision (first wavefront aberration distribution).

Figure 4:
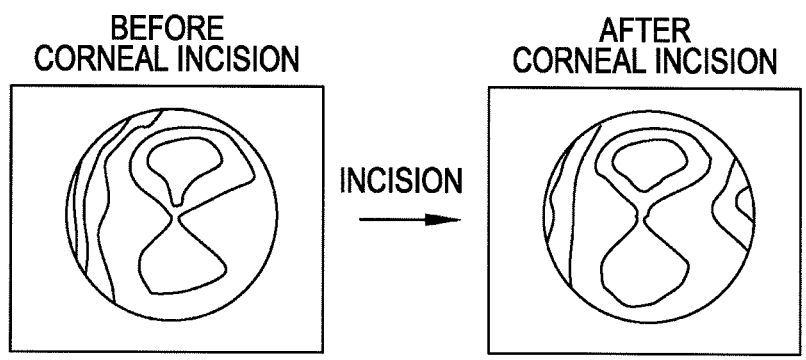
FIG. 4 illustrates change in aberration before and after incision of a cornea.

In the surgery, the cornea is incised to form the corneal incision for insertion of the TORIC IOL in the examinee's eye. Consequently, the corneal shape is changed. FIG. 4 illustrates change in aberration before and after incision of the cornea. Incision of the cornea causes aberration change in many portions of the entire cornea region corresponding to the pupil diameter. Thus, wavefront aberration distribution on the aforementioned entire region after incision (second wavefront aberration distribution) is calculated. Based on this second wavefront aberration distribution, the direction the astigmatic axis of the examinee's eye after formation of the corneal incision (after incision) (post-incision astigmatic axial direction) is calculated. This post-incision astigmatic axial direction is used as a guide at the time of inserting the TORIC IOL. This can improve correction accuracy with the TORIC IOL.

Calculation of Second Wavefront Aberration Distribution

Hereinafter, calculation of the post-incision astigmatic axial direction will be described. The memory 85 stores a table including incision aberration information corresponding to positions to form incisions and incision aberration information corresponding to the size of the incisions. An example of the incision aberration information includes information on two-dimensional change in wavefront aberration distribution on eyes corresponding to the positions to form the incisions and the size of the incisions (change information). An example of the change information includes high-order aberration.

In calculation of the wavefront aberration distribution, the surgeon first operates the operating unit 84. By this operation, information on the corneal incision to be formed on the cornea of the examinee's eye (corneal incision information) is input. Examples of the corneal incision information include information on the position to form the incision (corneal incision position) on the cornea and information on the size of the incision to be formed on the cornea (corneal incision size). The controller 80 obtains incision aberration information corresponding to the input corneal incision information from the memory 85. The controller 80 then calculates wavefront aberration distribution after formation of the incision (second wavefront aberration distribution) based on the first wavefront aberration distribution and the incision aberration information. That is, the controller 80 adds the incision aberration information to the first wavefront aberration distribution. Such addition allows the controller 80 to calculate predicted wavefront aberration distribution after formation of the corneal incision (second wavefront aberration distribution). The controller 80 then makes and outputs guide information to guide the intraocular lens surgery based on the second wavefront aberration distribution.

Creation of the aforementioned table will be described. For example, when an incision having the predetermined size is formed at the predetermined position of an examinee's eye, the controller 80 detects the change amount of the wavefront aberration distribution before and after formation of the incision. The controller 80 obtains incision aberration information based on the detection result. The controller 80 collects the change amounts of the wavefront aberration distribution corresponding to the positions of incisions and the size of the incisions by surgeries for many examinees' eyes. Therefore, the controller 80 creates a table including two-dimensional change in wavefront aberration distribution on eyes corresponding to the positions of the incisions and the size of the incisions (incision aberration information table).

After calculation of the second wavefront aberration distribution (after correction of the result of measurement of wavefront aberration), the controller 80 calculates S (spherical diopter power), C (cylindrical diopter power), and A (astigmatic axial direction (astigmatic axial angle)) of the examinee's eye based on a wavefront aberration component of the second wavefront aberration distribution using a Zernike polynomial. Therefore, the post-incision astigmatic axial direction can be calculated.

Figure 5:
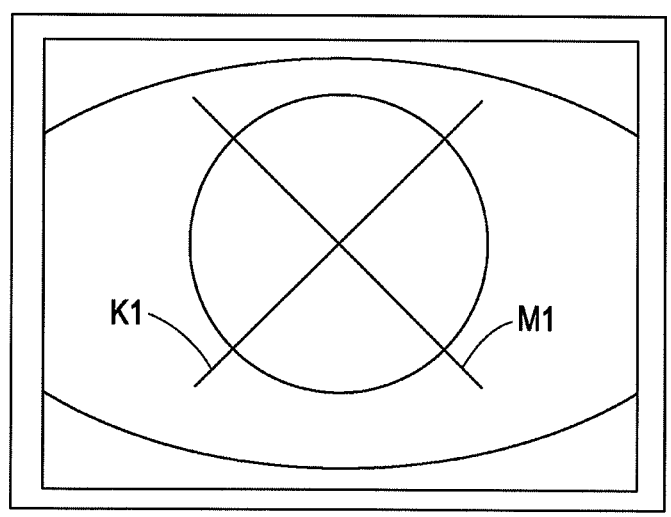
FIG. 5 illustrates an example of a display screen of a monitor.

FIG. 5 illustrates an example of a display screen of the monitor 70. In the present apparatus, the controller 80 calculates the post-incision astigmatic axial direction based on the second wavefront aberration distribution. The controller 80 then outputs information to the monitor 70. Here, the information indicates the post-incision astigmatic axial direction (post-incision astigmatic axis information) and serves as guide information for the intraocular lens inserting surgery. The post-incision astigmatic axis information is used as a guide to arrange the TORIC IOL in the eye, for example.

For example, the controller 80 superimposes and displays a target indicating the post-incision astigmatic axial direction (corneal astigmatic axis target: refer to the line K1 in FIG. 5) on the anterior segment image (observation image) using the post-incision astigmatic axis information. This anterior segment image is captured (observed) by the imaging optical system 30. The controller 80 derives a display angle of the line K1 and superimposes and displays the line K1 on the anterior segment image so that the line K1 passes the center of the placido target (optical axis of the present apparatus). The corneal astigmatic axis target (line K1) is displayed to indicate the strong principal meridian direction of the cornea of the eye E, for example.

Also, the controller 80 calculates the astigmatic axial direction (astigmatic axis) of the TORIC IOL at the time of insertion of the IOL based on the post-incision astigmatic axial direction. That is, the controller 80 calculates the astigmatic axial direction of the TORIC IOL based on astigmatic axis information of the IOL per manufacturer stored in the memory 85 in advance.

The controller 80 then displays on the monitor 70 a lens astigmatic axis target indicating the astigmatic axial direction of the TORIC IOL to be inserted (refer to the line M1 in FIG. 5) as well as the corneal astigmatic axis target (refer to the line K1 in FIG. 5). Thus, the surgeon can insert the TORIC IOL in the examinee's eye while confirming the lens astigmatic axis target. That is, the surgeon can arrange the TORIC IOL at an appropriate position in the examinee's eye easily. It is to be noted that shapes of the targets K1 and M1 are not limited to lines. For example, the controller 80 may display a graphic formed in an IOL shape on the monitor 70. In this case, the controller 80 may adjust a display angle of the graphic in accordance with the corneal astigmatic axis target. In the above manner, the controller 80 generates a graphic indicating the post-incision astigmatic axis information. The controller 80 then superimposes and displays this graphic on the anterior segment image captured by the imaging optical system 30.

In this manner, in the present apparatus, the controller 80 detects change in wavefront aberration distribution before and after formation of the corneal incision in order to derive overall change of the cornea region corresponding to the pupil diameter caused by formation of the corneal incision. The controller 80 then calculates the post-incision astigmatic axial direction using the result of detection of the wavefront aberration distribution. This can improve accuracy of calculation of the post-incision astigmatic axial direction. The controller 80 also detects overall change in the cornea region corresponding to the pupil diameter using change in the wavefront aberration distribution. Thus, the post-incision astigmatic axial direction of an examinee's eye with irregular astigmatism can be calculated accurately. The surgeon then arranges (inserts) the TORIC IOL in the examinee's eye based on the calculated post-incision astigmatic axial direction. Accordingly, correction accuracy with the TORIC IOL is improved.

Measurement of Ocular Axial Length

In measurement of the ocular axial length, the surgeon moves the present apparatus in up-down, right-left, and front-back directions using an operating unit such as a joystick (not shown) while looking at an alignment state of the examinee's eye displayed on the monitor 70. Therefore, the surgeon places the present apparatus at the predetermined position relative to the examinee's eye E.

After completion of the alignment, a trigger signal to start measurement is output automatically or manually. The controller 80 then turns on the measurement light source 1. Thus, measurement light is emitted to the examinee's eye by the ocular axial length measuring unit 10. The measurement light is reflected on the examinee's eye, and the reflected light enters the light receiving device of the ocular axial length measuring unit 10. The controller 80 calculates the ocular axial length based on a light receiving signal output from the light receiving device and timing at which interference light has been detected by the light receiving device. The calculated ocular axial length is used at the time of calculation of the diopter power of the IOL to be inserted in the examinee's eye by the IOL calculating formula.

Modification Examples

In the present embodiment, the controller 80 calculates the post-incision astigmatic axial direction using the result of measurement of the corneal shape. The present embodiment is not limited thereto. Alternatively, the controller 80 can calculate the diopter power of the intraocular lens using the second wavefront aberration distribution (wavefront aberration distribution after formation of the incision) calculated in the above manner. That is, the controller 80 substitutes the result of measurement of the corneal shape obtained as described above into the IOL calculating formula. By doing so, accuracy of calculation of the diopter power of the IOL can be improved. For example, the controller 80 can calculate the corneal curvature based on the second wavefront aberration distribution and calculate the diopter power of the IOL by a ray tracing method (ray simulation) based on the calculated corneal curvature.

In the present embodiment, the corneal incision information includes information on the position to form the incision on the cornea (corneal incision position) and information on the size of the incision to be formed on the cornea (corneal incision size). Based on this corneal incision information, the controller 80 obtains the incision aberration information. However, the present embodiment is not limited thereto. Alternatively, the corneal incision information may include at least either the information on the corneal incision position or the information on the corneal incision size. The controller 80 obtains the incision aberration information based on at least either one of these. The controller 80 calculates the second wavefront aberration distribution based on the first wavefront aberration distribution and the incision aberration information.

Also, anterior segment information may be obtained by an anterior segment measuring unit, and the second wavefront aberration distribution may be calculated based on the wavefront aberration before incision, the incision aberration information, and the anterior segment information. For example, the controller 80 obtains the incision aberration information based on information on any one of an eye pressure value, corneal thickness, a curvature radius of a corneal posterior surface, and a corneal diameter in addition to the corneal incision position and the corneal incision size. By doing so, incision aberration information in which the corneal incision position, the corneal thickness, and the like are considered is obtained. Accordingly, fluctuation of the second wavefront aberration distribution caused by change in the corneal thickness and the like is avoided. Of course, the incision aberration information may be obtained from combination of the aforementioned plural kinds of information. In this case, examples of the anterior segment measuring unit include an anterior segment OCT capable of obtaining information on a shape of the anterior segment and a Scheimpflug anterior segment tomographic image imaging apparatus.

Also, eye pressure information of the examinee's eye may be obtained by a tonometer, and the second wavefront aberration distribution may be calculated based on the wavefront aberration before incision, the incision aberration information, and the eye pressure information. Therefore, correction can be made on fluctuation of the second wavefront aberration distribution caused by the degree of the eye pressure.

Meanwhile, the post-incision astigmatic axial direction calculated as described above may be associated with a marker and information such as a scleral blood vessel, an iris pattern, a fundus image, and a corneal thickness profile and may be stored in the memory 85. This can be used as guide information for arrangement of the TORIC IOL.

In the present embodiment, the controller 80 may correct the angle to display (generate) the guide information (for example, the corneal astigmatic axis target) based on torsion information of the eye obtained by the corneal shape measuring unit 5. This can improve accuracy of the display angle. Also, the controller 80 may image a fundus blood vessel pattern before incision. In this case, the controller 80 may obtain the torsion information of the eye based on the fundus blood vessel pattern and correct the angle to display the guide information. Of course, the controller 80 may obtain the torsion information of the eye while observing the fundus blood vessel pattern during the surgery. In this case, the controller 80 may correct the angle to display the guide information to navigate the surgeon.

In the present embodiment, the guide information (guide pattern such as the corneal astigmatic axis target) is displayed as well as the lens astigmatic axis target indicating the astigmatic axis of the TORIC IOL to be inserted in the examinee's eye. However, the present embodiment is not limited thereto. Alternatively, the controller 80 may display either one of the targets on the monitor 70. Alternatively, the controller 80 may be configured to display neither of them. In this case, for example, the controller 80 may display a scale on the anterior segment image and display the calculated angle information (angle) of the post-incision astigmatic axial direction. Of course, the controller 80 may be configured so that whether or not the guide pattern is to be displayed can be selected.

In the present embodiment, the controller 80 calculates the second wavefront aberration distribution and thereafter calculates the post-incision astigmatic axial direction. The controller 80 then sets a position to arrange the TORIC IOL based on the post-incision astigmatic axial direction. However, the present embodiment is not limited thereto. Alternatively, the controller 80 may be configured to calculate an angle to arrange the TORIC IOL that causes the wavefront aberration to have a desired aberration amount at the time of insertion of the TORIC IOL (for example, an angle that causes the aberration to be the smallest). For example, after calculating the second wavefront aberration distribution based on the corneal incision information, the controller 80 may perform simulation in which the astigmatic axis of the TORIC IOL is rotated to detect wavefront aberration in accordance with a rotating position of the TORIC IOL. The controller 80 then obtains a rotating position that causes the wavefront aberration to be the smallest. In this case, the controller 80 may calculate (predict) wavefront aberration distribution in the examinee's eye in which the TORIC-Intraocular lens has been inserted (third wavefront aberration distribution) based on the rotating position information (information on the arrangement angle) of the TORIC IOL input by the surgeon, for example. In this case, the operating unit 84 allows input of the angle to arrange the TORIC-Intraocular lens (information on the arrangement angle). Alternatively, the controller 80 may calculate the third wavefront aberration distribution per rotating position (for example, per degree) of the TORIC IOL and derive a rotating position that allows for acquisition of a value close to a desired aberration amount.

Meanwhile, the technique of the present disclosure can be applied to simulation of how a view is at the time of insertion of the IOL. For example, the controller 80 calculates (predicts) wavefront aberration distribution in the examinee's eye in which the TORIC-Intraocular lens has been inserted (third wavefront aberration distribution) by calculation processing in which the aberration distribution of the TORIC IOL is added to the second wavefront aberration distribution obtained as described above. The controller 80 derives a point spread function (PSF) using this third wavefront aberration distribution. The controller 80 thereafter makes the obtained PSF and predetermined targets (entire ETDRS, respective items of scenery) subjected to image processing (convolution integration). By doing so, the controller 80 obtains a simulation image on how the predetermined targets are formed on a retinal surface of the examinee's eye at the time of insertion of the TORIC IOL in the examinee's eye. The controller 80 then displays on the monitor 70 simulation images on plural kinds of TORIC IOL. In this case, aberration information corresponding to the plural kinds of TORIC IOL is stored in the memory 85 in advance (for example, the name of a manufacturer, diopter power, and data in accordance with a kind of a lens of each TORIC IOL are stored).

In the above simulation, when a TORIC IOL is selected, the controller 80 rotates the astigmatic axis of the selected TORIC IOL and obtains information on a rotating position that allows for acquisition of a desired aberration amount. This information is displayed on the monitor 70.

In the present embodiment, the controller 80 calculates the pupil diameter of the examinee's eye. The controller 80 also derives the wavefront aberration distribution in the cornea region corresponding to the calculated pupil diameter. However, the present embodiment is not limited thereto. Alternatively, the controller 80 may use wavefront aberration distribution corresponding to an entire area of the cornea as the first wavefront aberration distribution of the cornea without depending on the pupil diameter.

In the present embodiment, the corneal shape measuring unit 5 including the placido ring projecting optical system 40 is used. The anterior segment image is used as an examinee's eye image. However, the present embodiment is not limited thereto. Alternatively, an optical coherence tomography device for photographing an anterior segment tomographic image (cross-sectional image) may be used, for example. In this case, an anterior segment tomographic image is obtained as an examinee's eye image at a plurality of scan positions. Therefore, a three-dimensional image is obtained. Then, the first wavefront aberration distribution is detected from the three-dimensional image.

Also, an apparatus that projects slit light to the anterior segment of the examinee's eye and obtains an anterior segment cross-sectional image by a Scheimpflug camera may be used. In this case, a three-dimensional image of the anterior segment is obtained by photographing the anterior segment while rotating the Scheimpflug camera. The first wavefront aberration distribution is then detected from the three-dimensional image. At this time, displacement correction may be performed per predetermined rotating angle. This allows the three-dimensional image of the anterior segment to be obtained accurately. Thus, accuracy of detection of the first wavefront aberration distribution is improved. Meanwhile, in the displacement correction (displacement correction processing), displacement in the direction perpendicular to an imaging surface (slit cross-section) is detected. Based on the detection result, displacement is corrected.

Also, in the present embodiment, the controller 80 may control almost all processing in the present apparatus. Also, the present embodiment is not limited thereto. Alternatively, a program to perform these processing (ophthalmic analysis software) may be stored in a recording medium, and an information processing device (such as a computer) that can read out this program may be used instead of the controller 80.

In this configuration, a calculating unit (a CPU or an MPU) of the information processing device reads out the program stored in the recording medium to execute the processing. Therefore, it can be said that this program itself performs the processing.

Here, as the aforementioned information processing device, a general computer (such as a work station or a personal computer), or a function expansion board or a function expansion unit to be provided in the computer, can be used.

Also, the aforementioned program includes program codes (an execution format program, an intermediate code program, a source program, and the like) of the software that performs the processing. This program may be used alone or may be combined with another program (an OS or the like). The program may also be read out from the recording medium, thereafter be stored once in a memory (a RAM or the like) in the device, thereafter be read out again, and be executed.

Also, the recording medium in which the program is to be stored may be one that can be separated easily from the information processing device or one that is fixed (attached) to the device. The recording medium may also be one connected to the device as an external storage unit.

Examples of media applicable to the recording medium include: magnetic tape such as video tape and cassette tape; magnetic disks such as a floppy (registered trademark) disk, an MD, and a hard disk; a magneto-optical disk such as an MO; optical disks such as a CD, a DVD, and a BD; memory cards such as an IC card and an optical card; and semiconductor memories such as a mask ROM, an EPROM, an EEPROM, a flash ROM, and a USB memory.

Also, a recording medium connected to the information processing device via a network (intranet, Internet, or the like) may be used. In this case, the information processing device obtains the program by download via the network. That is, the aforementioned program may be obtained via a transmission medium (a medium that holds a program in a flexible manner) such as a network (one that is connected to a wired or wireless line). Meanwhile, a program to perform download is preferably stored in the information processing device (or in a transmission-side device and a reception-side device) in advance. Also, the aforementioned recording medium is a non-transitory medium.

Furthermore, FIG. 3A also illustrates a state of the pupil image stored in the memory 85. FIG. 3B also illustrates an image signal along the scanning line L. To derive edges between a pupil (dark part) and an iris (bright part), signal waveform illustrated in FIG. 3B may first be subjected to differential processing. The signal waveform at this time is one illustrated in FIG. 3C. These signals are positive and negative signals. Additionally, when these are squared, they become positive value signals illustrated in FIG. 3D. In FIG. 3D, when edges of the first waveform signal having the height e1 and the last waveform signal having the height e2 are defined as points that are ½ of the respective heights (amplitude) for example, pixel positions n1 and n2 are coordinate positions of the edges on the scanning line L.

As for photographing of the anterior segment image to be used for pupil detection, both/either the pupil size in a bright field state and/or the pupil size in a dark field state may be detected.

Also, after correction of the result of measurement of the wavefront aberration, the controller 80 may calculate respective values of S (spherical diopter power), C (cylindrical diopter power), and A (astigmatic axial direction (astigmatic axial angle)) based on the wavefront aberration measurement result (wavefront aberration component) using a Zernike polynomial. By doing so, the astigmatic axial direction in the examinee's eye after formation of the corneal incision can be calculated.

Also, in the present apparatus, change in the corneal shape caused by formation of the corneal incision may be regarded as overall change in the corneal shape due to wavefront aberration. In this case, when the astigmatic axial direction of the examinee's eye after formation of the corneal incision is calculated using the measurement result, calculation accuracy is improved. Also, because the change is regarded as overall change in the corneal shape due to wavefront aberration, the astigmatic axis of the examinee's eye with irregular astigmatism can be calculated accurately. Because arrangement of the TORIC IOL is performed based on the calculated astigmatic axial direction at the time of insertion of the TORIC IOL, correction accuracy is improved.

Also, in the wavefront aberration measured by the corneal shape measuring unit 5 by calculating the pupil diameter of the examinee's eye by the controller 80, a wavefront aberration region corresponding to a region of the calculated pupil diameter may be calculated as wavefront aberration.

It is to be noted that the present disclosure is not limited to the apparatus described in the present embodiment. For example, ophthalmic analysis software (program) functioning as the aforementioned embodiment is supplied to a system or an apparatus via a network or various recording media. Subsequently, a computer (for example, a CPU) of the system or the apparatus can read out and execute the program.

Also, the ophthalmic apparatus of the present disclosure may be first to thirteenth ophthalmic apparatuses described below.

A first ophthalmic apparatus includes a corneal aberration measuring unit configured to measure wavefront aberration of a cornea of an examinee's eye, an input unit configured to input causing corneal incision information on a corneal incision to be formed on the cornea of the examinee's eye, and a calculation controller, wherein the calculation controller obtains incision aberration information corresponding to the corneal incision information input via the input unit, calculates wavefront aberration after formation of the incision based on wavefront aberration before incision measured by the corneal aberration measuring unit and the incision aberration information, and outputs guide information that guides an intraocular lens surgery based on the wavefront aberration obtained by the calculation controller.

A second ophthalmic apparatus is one according to the first ophthalmic apparatus wherein the corneal incision information is at least either corneal incision position information or corneal incision size information, and the calculation controller obtains the incision aberration information corresponding to at least either the corneal incision position information or the corneal incision size information input via the input unit and calculates the wavefront aberration after formation of the corneal incision based on the wavefront aberration before the incision measured by the corneal aberration measuring unit and the incision aberration information.

A third ophthalmic apparatus is one according to the second ophthalmic apparatus wherein the calculation controller calculates the astigmatic axial direction of the examinee's eye based on the wavefront aberration after formation of the corneal incision and outputs calculated astigmatic axis information of the examinee's eye.

A fourth ophthalmic apparatus is one according to the third ophthalmic apparatus further including an observing optical system configured to observe the examinee's eye, wherein the calculation controller generates a graphic indicating the calculated astigmatic axis information and superimposes and displays the graphic on an observation image observed by the observing optical system.

A fifth ophthalmic apparatus is one according to the first ophthalmic apparatus wherein the calculation controller calculates diopter power of an intraocular lens using the wavefront aberration after formation of the corneal incision.

A sixth ophthalmic apparatus is one according to the first ophthalmic apparatus wherein the calculation controller obtains change information on two-dimensional change in wavefront aberration distribution on the eye corresponding to the corneal incision information input via the input unit and calculates the wavefront aberration distribution after formation of the corneal incision based on the wavefront aberration distribution before the incision measured by the corneal aberration measuring unit and the change information.

A seventh ophthalmic apparatus is one according to the first ophthalmic apparatus wherein the change information includes high-order aberration.

An eighth ophthalmic apparatus is one according to the first ophthalmic apparatus further including a pupil diameter measuring unit configured to measure a pupil diameter of the examinee's eye, wherein, in the wavefront aberration measured by the corneal aberration measuring unit, the calculation controller calculates wavefront aberration corresponding to a region of the pupil diameter calculated by the pupil diameter measuring unit as wavefront aberration.

A ninth ophthalmic apparatus is one according to the first ophthalmic apparatus further including an anterior segment measuring unit configured to obtain anterior segment information, wherein the calculation controller calculates the wavefront aberration after formation of the corneal incision based on the wavefront aberration before the incision measured by the corneal aberration measuring unit, the incision aberration information, and the anterior segment information obtained by the anterior segment measuring unit.

A tenth ophthalmic apparatus is one according to the first ophthalmic apparatus wherein the calculation controller further calculates predicted wavefront aberration after the surgery based on the calculated wavefront aberration after formation of the corneal incision and aberration information of a TORIC-Intraocular lens.

An eleventh ophthalmic apparatus is one according to the tenth ophthalmic apparatus wherein the calculation controller calculates the predicted wavefront aberration in accordance with an angle to arrange the TORIC-Intraocular lens.

A twelfth ophthalmic apparatus is one according to the tenth ophthalmic apparatus further including an image processor configured to obtain an image for a simulation of how a view is based on the predicted wavefront aberration.

A thirteenth ophthalmic apparatus is one according to the tenth ophthalmic apparatus wherein the input unit is also provided as an input unit configured to change the angle to arrange the TORIC-Intraocular lens.

Also, a recording medium having an ophthalmic program stored therein according to the present disclosure may be a first recording medium described below. This first recording medium has an ophthalmic program stored therein. This ophthalmic program is executed by a controller configured to control operation of an ophthalmic apparatus to make the ophthalmic apparatus execute a wavefront aberration measuring process of measuring wavefront aberration from a corneal shape obtained by a corneal shape measuring unit, an inputting process of inputting corneal incision position information and corneal incision size information, a wavefront aberration calculating process of retrieving a wavefront aberration change amount from a memory having a wavefront aberration correction amount for correction of wavefront aberration generated per corneal incision position information and corneal incision size information stored therein based on the corneal incision position information and corneal incision size information output in the inputting process and adding the wavefront aberration change amount to the wavefront aberration measured in the wavefront aberration measuring process, and a guiding process of outputting guide information that guides an intraocular lens surgery based on a result of measurement of the wavefront aberration obtained in the wavefront aberration calculating process.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An ophthalmic apparatus comprising:
   an input unit configured to obtain corneal incision information that is information on a corneal incision to be formed on a cornea of an examinee's eye;
   an imaging device configured to capture an examinee's eye image; and
   a controller, wherein
   the controller is configured to
      calculate a first wavefront aberration distribution that is a wavefront aberration distribution of the cornea before incision on the examinee's eye based on the examinee's eye image,
      obtain incision aberration information corresponding to the corneal incision information,
      calculate a second wavefront aberration distribution that is a wavefront aberration distribution after formation of the incision based on the first wavefront aberration distribution and the incision aberration information, and
      output guide information that guides an intraocular lens surgery based on the second wavefront aberration distribution.

2. The ophthalmic apparatus according to claim 1, wherein the corneal incision information includes at least either information on a corneal incision position or information on a corneal incision size.

3. The ophthalmic apparatus according to claim 2, wherein the controller calculates a post-incision astigmatic axial direction that is an astigmatic axial direction of the examinee's eye after the incision based on the second wavefront aberration distribution and outputs information on this post-incision astigmatic axial direction as the guide information.

4. The ophthalmic apparatus according to claim 3, wherein the controller generates a graphic indicating the information on the post-incision astigmatic axial direction as the guide information and superimposes and displays this graphic on the examinee's eye image.

5. The ophthalmic apparatus according to claim 1, wherein the controller calculates diopter power of an intraocular lens using the second wavefront aberration distribution.

6. The ophthalmic apparatus according to claim 1, wherein the controller calculates the second wavefront aberration distribution based on change information on two-dimensional change in wavefront aberration distribution on the eye included in the incision aberration information and the first wavefront aberration distribution.

7. The ophthalmic apparatus according to claim 6, wherein the change information includes high-order aberration.

8. The ophthalmic apparatus according to claim 1, wherein the controller calculates a pupil diameter of the examinee's eye from the examinee's eye image and calculates a wavefront aberration distribution in a cornea region corresponding to the pupil diameter as the first wavefront aberration distribution.

9. The ophthalmic apparatus according to claim 1, wherein the examinee's eye image is an anterior segment image, and the controller calculates the second wavefront aberration distribution based on the first wavefront aberration distribution, the incision aberration information, and information on the anterior segment image.

10. The ophthalmic apparatus according to claim 1, wherein
the intraocular lens is a TORIC-Intraocular lens, and
the controller further calculates a third wavefront aberration distribution that is a wavefront aberration distribution in the examinee's eye in which the TORIC-Intraocular lens has been inserted based on the second wavefront aberration distribution and an aberration distribution of the TORIC-Intraocular lens.

11. The ophthalmic apparatus according to claim 10, wherein
the controller calculates the third wavefront aberration distribution in accordance with an angle to arrange the TORIC-Intraocular lens.

12. The ophthalmic apparatus according to claim 10, wherein
the controller obtains a simulation image on how a predetermined target is formed on a retinal surface of the examinee's eye at the time of insertion of the TORIC-Intraocular lens in the examinee's eye based on the third wavefront aberration distribution.

13. The ophthalmic apparatus according to claim 11, wherein
the input unit further allows input of the angle to arrange the TORIC-Intraocular lens.

14. A non-transitory recording medium having stored therein an ophthalmic program configured to make an information processing device function as the controller in the ophthalmic apparatus according to claim 1.

15. A non-transitory recording medium having stored therein an ophthalmic program configured to make a controller configured to control operation of an ophthalmic apparatus execute:
calculation of a first wavefront aberration distribution that is a wavefront aberration distribution of a cornea before incision on an examinee's eye based on an examinee's eye image;
acquisition of incision aberration information corresponding to corneal incision information on a corneal incision to be formed on the cornea of the examinee's eye;
calculation of a second wavefront aberration distribution that is a wavefront aberration distribution after formation of the incision based on the first wavefront aberration distribution and the incision aberration information; and
output of guide information that guides an intraocular lens surgery based on the second wavefront aberration distribution.

* * * * *